(12) United States Patent
Reichelt et al.

(10) Patent No.: US 8,471,020 B2
(45) Date of Patent: Jun. 25, 2013

(54) PERYLENE-BASED SEMICONDUCTING MATERIALS

(75) Inventors: Helmut Reichelt, Neustadt (DE); Thomas Geβner, Heidelberg (DE); Klaus Müllen, Köln (DE); Chen Li, Mainz (DE); Glauco Battagliarin, Mainz (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 13/412,023

(22) Filed: Mar. 5, 2012

(65) Prior Publication Data

US 2012/0226042 A1     Sep. 6, 2012

Related U.S. Application Data

(60) Provisional application No. 61/448,669, filed on Mar. 3, 2011.

(51) Int. Cl.
*C07D 471/08*     (2006.01)
*H01L 51/00*      (2006.01)

(52) U.S. Cl.
USPC ............................. 546/37; 313/498; 313/504

(58) Field of Classification Search
USPC ..................... 546/37; 313/498, 504
See application file for complete search history.

(56) References Cited

U.S. PATENT DOCUMENTS

| | | | |
|---|---|---|---|
| 7,282,275 B2 | 10/2007 | Wolk et al. | |
| 7,326,956 B2 | 2/2008 | Shukla et al. | |
| 7,355,198 B2 | 4/2008 | Suh et al. | |
| 7,671,202 B2 | 3/2010 | Marks et al. | |
| 2005/0176970 A1 | 8/2005 | Marks | |
| 2008/0177073 A1 | 7/2008 | Facchetti et al. | |
| 2008/0185577 A1 | 8/2008 | Facchetti et al. | |
| 2008/0223444 A1 | 9/2008 | Marder et al. | |
| 2010/0319778 A1 | 12/2010 | Kastler et al. | |
| 2011/0136333 A1 | 6/2011 | Facchetti et al. | |

FOREIGN PATENT DOCUMENTS

| | | |
|---|---|---|
| WO | 2005124453 | 12/2005 |
| WO | 2008063609 | 5/2008 |
| WO | 2008085942 | 7/2008 |
| WO | 2009098252 | 8/2009 |
| WO | 2009144205 | 12/2009 |

OTHER PUBLICATIONS

Battagliarin, G. et al.: Efficient tuning of LUMO levels of 2,5,8,11-substituted perylenediimides via Copper catalyzed reactions. Organic Letters, vol. 13, pp. 3399-3401, 2011.*
Satomi Nakazono, et al., Organic Letters, 2009, vol. 11, No. 23, pp. 5426-5429.
Soichiro Kawamorita, et al., Journal of American Chemical Society, 2009, vol. 131, pp. 5058-5059.
Ibraheem A. I. Mkhalid, et al., Chemical Revisions, 2009, vol. 110, pp. 890-931.
Carl W. Liskey, et al., Journal of American Chemical Society, 2010, vol. 132, pp. 11389-11391.

* cited by examiner

*Primary Examiner* — Charanjit Aulakh
(74) *Attorney, Agent, or Firm* — Shiela A. Loggins (57) ABSTRACT

The present invention provides a compound of formula (1)

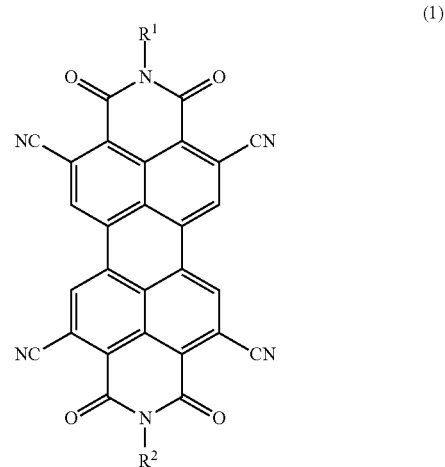

The compound of formula (1) is suitable for use as semiconducting material, in particular in electronic devices.

8 Claims, 3 Drawing Sheets

| | Hexamethyldisilazane | | Au/Ta Source Electrode |
| | Highly Doped Silicon Gate | | Au/Ta Drain Electrode |
| | Silicon Dioxide Dielectric Layer | | |
| | 1b as Semiconducting Layer | | |

Figure 1: Bottom-gate organic field effect transistor of example 5.

Figure 2: Compound 1b, transfer curves.

Figure 3: compound 1b: charge carrier mobility $\mu_{sat}$ [cm$^2$/Vs] in relation to gate voltage $V_{SG}$ [V]

PERYLENE-BASED SEMICONDUCTING MATERIALS

This application claims the benefit of U.S. Provisional Application No. 61/448,669 filed Mar. 3, 2011 herein incorporated entirely by reference.

DESCRIPTION

Organic semiconducting materials can be used in electronic devices such as organic photovoltaic (OPV) cells, organic field-effect transistors (OFETs) and organic light emitting diodes (OLEDs).

For efficient and long lasting performance, it is desirable that the organic semiconducting material-based devices show high charge carrier mobility and high stability, in particular towards oxidation, under ambient conditions.

Furthermore, it is desirable that the organic semiconducting materials are compatible with liquid processing techniques as liquid processing techniques are convenient from the point of processability, and thus allow the production of low cost organic semiconducting material-based electronic devices. In addition, liquid processing techniques are also compatible with plastic substrates, and thus allow the production of light weight and flexible organic semiconducting material-based electronic devices.

The use of perylene-based organic semiconducting materials in electronic devices is known in the art.

U.S. Pat. No. 7,282,275 B2 describes a composition that includes a first compound of formula $[EC-]_n-Ar^1$ (I), wherein
$A^1$ is a first aromatic core and is a divalent, trivalent or tetravalent radical of a long list of formulae, including that is unsubstituted or substituted with a long list of substituents, including fluoro and cyano,
EC is a first end capping group and is a monovalent radical of a long list of formulae,
n is an integer of 2 to 4
Z is NH or CH$_2$, and
a second compound having an aromatic radical that comprises the first aromatic core of the first compound, a second end capping group that comprises the first end capping group of the first compound, a divalent radical that comprises a divalent radical of the first end capping group, or a combination thereof,
wherein the composition is amorphous and solution processible.

Also provided is an electronic device including the composition.

U.S. Pat. No. 7,355,198 B2 describes am organic thin film transistor (OFET), which interposes an organic acceptor film between source and drain electrodes and an organic semiconductor film. The organic semiconductor film is formed of pentacene. In particular, the organic acceptor film is formed of at least one electron withdrawing material selected from a long list of compounds, including N,N'-bis(di-tert-butyphenyl)-3,4,9,10-perylenedicarboxylmide.

U.S. Pat. No. 7,326,956 B2 describes a thin film transistor comprising a layer of organic semiconductor material comprising tetracarboxylic diimide 3,4,9,10-perylene-based compound having attached to each of the imide nitrogen atoms a carbocyclic or heterocyclic aromatic ring system substituted with one or more fluorine containing groups. In one embodiment the fluorine-containing N,N'-diaryl perylene-based tetracarboxylic diimide compound is represented by the following structure:

wherein $A^1$ and $A^2$ are independently carbocyclic and/or heterocyclic aromatic ring systems comprising at least one aromatic ring in which one or more hydrogen atoms are substituted with at least one fluorine-containing group. The perylene nucleus can be optionally substituted with up to eight independently selected X groups, wherein n is an integer from 0 to 8. The X substituent groups on the perylene can include a long list of substituents, including halogens such as fluorine or chlorine, and cyano.

U.S. Pat. No. 7,671,202 B2 describes n-type semiconductor compounds of formula wherein each $R^1$ to $R^8$, $R^{11}$ and $R^{12}$ can be independently selected from H, an electron-withdrawing substituent and a moiety comprising such substituent. Electron-withdrawing substitutents include a long list of substituents, including cyano. $R^9$ and $R^{10}$ are independently selected from H, alkyl, substituted alkyl, cycloalkyl, substituted cycloalkyl, aryl, substituted aryl, polycyclic aryl and/or substituted polycyclic aryl moieties. At least one of $R^1$, $R^4$, $R^5$, $R^8$, $R^{11}$ and $R^{12}$ can be a cyano substituent. Such cyanated compounds can be di- or tetra-substituted as shown by the following structures:

WO 2005/124453 describes perylenetetracarboxylic diimide charge-transfer materials, for example a perylenetetracarboxylic diimide charge-transfer material having formula wherein Y in each instance can be independently selected from H, CN, acceptors, donors and a polymerizable group; and X in each instance can be independently selected from a large group of listed compounds.

WO 2008/063609 describes diimide-based semiconductor compounds. In a particular embodiment the compound can have formula wherein $R^1$ at each occurrence is independently selected from a long list of groups, including branched $C_{3-20}$-alkyl and branched $C_{3-20}$-alkenyl.

WO 2009/098252 describes semiconducting compounds having formula wherein $R^1$ and $R^2$ at each occurrence independently are selected from a large list of groups, including H, $C_{1-30}$-alkyl and $C_{2-30}$-alkenyl; and $R^3$, $R^4$, $R^5$ and $R^6$ are independently H or an electron-withdrawing group. In certain embodiments, at least one of $R^3$, $R^4$, $R^5$ and $R^6$ can be Br or cyano. For example, the semiconducting compound can include WO 2009/144205 describes bispolycyclic rylene-based semiconducting materials, for example S. Nakanzono, S. Easwaramoorthi, D. Kim, H. Shinokubo, A. Osuka *Org. Lett.* 2009, 11, 5426 to 5429 describes the preparation of 2,5,8,11 tetraarylated perylene tetracaroxylic acid bisimides from perylene tetracarboxylic acid bisimides It was the object of the present invention to provide new perylene-based semiconducting materials.

The object is solved by the compound of claim 1, the process of claim 2, the compound of claim 6, and the electronic device of claim 7.

The perylene-based semiconducting compound of the present invention is of formula (1)

wherein $R^1$ and $R^2$ are independently selected from the group consisting of H, $C_{1-30}$-alkyl, $C_{2-30}$-alkenyl, $C_{2-30}$-alkynyl, $C_{3-10}$-cycloalkyl, $C_{5-10}$-cycloalkenyl, 3-14 membered cycloheteroalkyl, $C_{6-14}$-aryl and 5-14 membered heteroaryl, wherein if $R^1$ or $R^2$ are $C_{1-30}$-alkyl, $C_{2-30}$-alkenyl or $C_{2-30}$-alkynyl, this $R^1$ or $R^2$ can be optionally substituted with 1 to 6 groups independently selected from the group consisting of halogen, —CN, —NO$_2$, —OH, $C_{1-10}$-alkoxy, —O—CH$_2$CH$_2$O—$C_{1-10}$-alkyl, —O—COR$^3$, —S—$C_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, $C_{3-10}$-cycloalkyl, 3-14 membered cycloheteroalkyl, $C_{6-14}$-aryl and 5-14 membered heteroaryl;

if $R^1$ or $R^2$ are $C_{3-10}$-cycloalkyl, $C_{5-10}$-cycloalkenyl or 3-14 membered cycloheteroalkyl, this $R^1$ or $R^2$ can be optionally substituted with 1 to 6 groups independently selected from the group consisting of halogen, —CN, —NO$_2$, —OH, C$_{1-10}$-alkoxy, —O—CH$_2$CH$_2$O—C$_{1-10}$-alkyl, —O—COR$^3$, —S—C$_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, C$_{1-10}$-alkyl, C$_{2-10}$-alkenyl, C$_{2-10}$-alkynyl, C$_{6-14}$-aryl and 5-14 membered heteroaryl;

if R$^1$ or R$^2$ are C$_{6-14}$-aryl or 5-14 membered heteroaryl, this R$^1$ or R$^2$ can be optionally substituted with 1 to 6 groups independently selected from the group consisting of halogen, —CN, —NO$_2$, —OH, C$_{1-10}$-alkoxy, —O—CH$_2$CH$_2$O—C$_{1-10}$-alkyl, —O—COR$^3$, —S—C$_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, C$_{1-10}$-alkyl, C$_{2-10}$-alkenyl, C$_{2-10}$-alkynyl, C$_{3-10}$-cycloalkyl, C$_{5-10}$-cycloalkenyl and 3-14 membered cycloheteroalkyl, wherein R$^3$ and R$^4$ are at each occurrence are independently from each other selected from the group consisting of C$_{1-10}$-alkyl, C$_{2-10}$-alkenyl, C$_{2-10}$-alkynyl, C$_{3-10}$-cycloalkyl, C$_{5-10}$-cycloalkenyl, 3-14 membered cycloheteroalkyl, C$_{6-14}$-aryl and 5-14 membered heteroaryl.

C$_{1-10}$-alkyl and C$_{1-30}$-alkyl can be branched or unbranched. Examples of C$_{1-10}$-alkyl are methyl, ethyl, n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl, n-(2-ethyl)hexyl, n-nonyl and n-decyl. Examples of C$_{3-8}$-alkyl are n-propyl, isopropyl, n-butyl, sec-butyl, isobutyl, tert-butyl, n-pentyl, neopentyl, isopentyl, n-(1-ethyl)propyl, n-hexyl, n-heptyl, n-octyl and n-(2-ethyl)hexyl. Examples of C$_{1-30}$-alkyl are C$_{1-10}$-alkyl, and n-undecyl, n-dodecyl, n-undecyl, n-dodecyl, n-tridecyl, n-tetradecyl, n-pentadecyl, n-hexadecyl, n-heptadecyl, n-octadecyl, n-nonadecyl and n-icosyl (C$_{20}$), n-docosyl (C$_{22}$), n-tetracosyl (C$_{24}$), n-hexacosyl (C$_{26}$), n-octacosyl (C$_{28}$) and n-triacontyl (C$_{30}$).

C$_{2-10}$-alkenyl and C$_{2-30}$-alkenyl can be branched or unbranched. Examples of C$_{2-10}$-alkenyl are vinyl, propenyl, cis-2-butenyl, trans-2-butenyl, 3-butenyl, cis-2-pentenyl, trans-2-pentenyl, cis-3-pentenyl, trans-3-pentenyl, 4-pentenyl, 2-methyl-3-butenyl, hexenyl, heptenyl, octenyl, nonenyl and docenyl. Examples of C$_{2-30}$-alkenyl are C$_{2-10}$-alkenyl, and linoleyl (C$_{18}$), linolenyl (C$_{18}$), oleyl (C$_{18}$), arachidonyl (C$_{20}$), and erucyl (C$_{22}$).

C$_{2-10}$-alkynyl and C$_{2-30}$-alkynyl can be branched or unbranched. Examples of C$_{2-10}$-alkynyl are ethynyl, 2-propynyl, 2-butynyl, 3-butynyl, pentynyl, hexynyl, heptynyl, octynyl, nonynyl and decynyl. Examples of C$_{2-30}$-alkynyl are C$_{2-10}$-alkynyl, and undecynyl, dodecynyl, undecynyl, dodecynyl, tridecynyl, tetradecynyl, pentadecynyl, hexadecynyl, heptadecynyl, octadecynyl, non-adecynyl and icosynyl (C$_{20}$).

Examples of C$_{3-10}$-cycloalkyl are preferably monocyclic C$_{3-10}$-cycloalkyls such as cyclopropyl, cyclobutyl, cyclopentyl, cyclohexyl, cycloheptyl and cyclooctyl, but include also polycyclic C$_{3-10}$-cycloalkyls such as decalinyl, norbornyl and adamantyl.

Examples of C$_{5-10}$-cycloalkenyl are preferably monocyclic C$_{5-10}$-cycloalkenyls such as cyclopentenyl, cyclohexenyl, cyclohexadienyl and cycloheptatrienyl, but include also polycyclic C$_{5-10}$-cycloalkenyls.

Examples of 3-14 membered cycloheteroalkyl are monocyclic 3-8 membered cycloheteroalkyl and polycyclic, for example bicyclic 7-12 membered cycloheteroalkyl.

Examples of monocyclic 3-8 membered cycloheteroalkyl are monocyclic 5 membered cycloheteroalkyl containing one heteroatom such as pyrrolidinyl, 1-pyrrolinyl, 2-pyrrolinyl, 3-pyrrolinyl, tetrahydrofuryl, 2,3-dihydrofuryl, tetrahydrothiophenyl and 2,3-dihydrothiophenyl, monocyclic 5 membered cycloheteroalkyl containing two heteroatoms such as imidazolidinyl, imidazolinyl, pyrazolidinyl, pyrazolinyl, oxazolidinyl, oxazolinyl, isoxazolidinyl, isoxazolinyl, thiazolidinyl, thiazolinyl, isothiazolidinyl and isothiazolinyl, monocyclic 5 membered cycloheteroalkyl containing three heteroatoms such as 1,2,3-triazolyl, 1,2,4-triazolyl and 1,4,2-dithiazolyl, monocyclic 6 membered cycloheteroalkyl containing one heteroatom such as piperidyl, piperidino, tetrahydropyranyl, pyranyl, thianyl and thiopyranyl, monocyclic 6 membered cycloheteroalkyl containing two heteroatoms such as piperazinyl, morpholinyl and morpholino and thiazinyl, monocyclic 7 membered cycloheteroalkyl containing one hereoatom such as azepanyl, azepinyl, oxepanyl, thiepanyl, thiapanyl, thiepinyl, and monocyclic 7 membered cycloheteroalkyl containing two hereoatom such as 1,2-diazepinyl and 1,3-thiazepinyl.

An example of a bicyclic 7-12 membered cycloheteroalkyl is decahydronaphthyl.

C$_{6-14}$-aryl can be monocyclic or polycyclic. Examples of C$_{6-14}$-aryl are monocyclic C$_6$-aryl such as phenyl, bicyclic C$_{6-10}$-aryl such as 1-naphthyl, 2-naphthyl, indenyl, indanyl and tetrahydronaphthyl, and tricyclic C$_{12-14}$-aryl such as anthryl, phenanthryl, fluorenyl and s-indacenyl.

5-14 membered heteroaryl can be monocyclic 5-8 membered heteroaryl, or polycyclic 7-14 membered heteroaryl, for example bicyclic 7-12 membered or tricyclic 9-14 membered heteroaryl.

Examples of monocyclic 5-8 membered heteroaryl are monocyclic 5 membered heteroaryl containing one heteroatom such as pyrrolyl, furyl and thiophenyl, monocyclic 5 membered heteroaryl containing two heteroatoms such as imidazolyl, pyrazolyl, oxazolyl, isoxazolyl, thiazolyl, isothiazolyl, monocyclic 5 membered heteroaryl containing three heteroatoms such as 1,2,3-triazolyl, 1,2,4-triazolyl and oxadiazolyl, monocyclic 5 membered heteroaryl containing four heteroatoms such as tetrazolyl, monocyclic 6 membered heteroaryl containing one heteroatom such as pyridyl, monocyclic 6 membered heteroaryl containing two heteroatoms such as pyrazinyl, pyrimidinyl and pyridazinyl, monocyclic 6 membered heteroaryl containing three heteroatoms such as 1,2,3-triazinyl, 1,2,4-triazinyl and 1,3,5-triazinyl, monocyclic 7 membered heteroaryl containing one heteroatom such as azepinyl, and monocyclic 7 membered heteroaryl containing two heteroatoms such as 1,2-diazepinyl.

Examples of bicyclic 7-12 membered heteroaryl are bicyclic 9 membered heteroaryl containing one heteroatom such as indolyl, isoindolyl, indolizinyl, indolinyl, benzofuryl, isobenzofuryl, benzothiophenyl and isobenzothiophenyl, bicyclic 9 membered heteroaryl containing two heteroatoms such as indazolyl, benzimidazolyl, benzimidazolinyl, benzoxazolyl, benzisooxazolyl, benzthiazolyl, benzisothiazolyl, furopyridyl and thienopyridyl, bicyclic 9 membered heteroaryl containing three heteroatoms such as benzotriazolyl, benzoxadiazolyl, oxazolopyridyl, isooxazolopyridyl, thiazolopyridyl, isothiazolopyridyl and imidazopyridyl, bicyclic 9 membered heteroaryl containing four heteroatoms such as purinyl, bicyclic 10 membered heteroaryl containing one heteroatom such as quinolyl, isoquinolyl, chromenyl and chromanyl, bicyclic 10 membered heteroaryl containing two heteroatoms such as quinoxalinyl, quinazolinyl, cinnolinyl, phthalazinyl, 1,5-naphthyridinyl and 1,8-naphthyridinyl, bicyclic 10 membered heteroaryl containing three heteroatoms such as pyridopyrazinyl, pyridopyrimidinyl and pyridopyridazinyl, and bicyclic 10 membered heteroaryl containing four heteroatoms such as pteridinyl.

Examples of tricyclic 9-14 membered heteroaryls are dibenzofuryl, acridinyl, phenoxazinyl, 7H-cyclopenta[1,2-b:3,4-b']dithiophenyl and 4H-cyclopenta[2,1-b:3,4-b']dithiophenyl.

Examples of halogen are —F, —Cl, —Br and —I.

Examples of $C_{1-10}$-alkoxy are methoxy, ethoxy, n-propoxy, isopropoxy, n-butoxy, sec-butoxy, isobutoxy, tert-butoxy, n-pentoxy, neopentoxy, isopentoxy, hexoxy, n-heptoxy, n-octoxy, n-nonoxy and n-decoxy.

Examples of $C_{2-5}$-alkylene are ethylene, propylene, butylene and pentylene.

Preferably, $R^1$ and $R^2$ are independently selected from the group consisting of H, $C_{1-30}$-alkyl, $C_{2-30}$-alkenyl, $C_{2-30}$-alkynyl, $C_{3-10}$-cycloalkyl, $C_{5-10}$-cycloalkenyl, 3-14 membered cycloheteroalkyl, wherein if $R^1$ or $R^2$ are $C_{1-30}$-alkyl, $C_{2-30}$-alkenyl or $C_{2-30}$-alkynyl, this $R^1$ or $R^2$ can be optionally substituted with 1 to 6 groups independently selected from the group consisting of halogen, —CN, —$NO_2$, —OH, $C_{1-10}$-alkoxy, —O—$CH_2CH_2$O—$C_{1-10}$-alkyl, —O—$COR^3$, —S—$C_{1-10}$-alkyl, —$NH_2$, —$NHR^3$, —$NR^3R^4$, —NH—$COR^3$, —COOH, —COORS, —$CONH_2$, —$CONHR^3$, —$CONR^3R^4$, —CO—H, —$COR^3$, $C_{3-10}$-cycloalkyl, 3-14 membered cycloheteroalkyl, $C_{6-14}$-aryl and 5-14 membered heteroaryl;

if $R^1$ or $R^2$ are $C_{3-10}$-cycloalkyl, $C_{5-10}$-cycloalkenyl or 3-14 membered cycloheteroalkyl, this $R^1$ or $R^2$ can be optionally substituted with 1 to 6 groups independently selected from the group consisting of halogen, —CN, —$NO_2$, —OH, $C_{1-10}$-alkoxy, —O—$CH_2CH_2$O—$C_{1-10}$-alkyl, —O—$COR^3$, —S—$C_{1-10}$-alkyl, —$NH_2$, —$NHR^3$, —$NR^3R^4$, —NH—$COR^3$, —COOH, —COORS, —$CONH_2$, —$CONHR^3$, —$CONR^3R^4$, —CO—H, —$COR^3$, $C_{1-10}$-alkyl, $C_{2-10}$-alkenyl, $C_{2-10}$-alkynyl, $C_{6-14}$-aryl and 5-14 membered heteroaryl;

wherein $R^3$ and $R^4$ are at each occurrence are independently from each other selected from the group consisting of $C_{1-10}$-alkyl, $C_{2-10}$-alkenyl, $C_{2-10}$-alkynyl, $C_{3-10}$-cycloalkyl, $C_{5-10}$-cycloalkenyl, 3-14 membered cycloheteroalkyl, $C_{6-14}$-aryl and 5-14 membered heteroaryl.

More preferably, $R^1$ and $R^2$ are independently selected from the group consisting of H, $C_{1-30}$-alkyl, $C_{2-30}$-alkenyl, wherein if $R^1$ or $R^2$ are $C_{1-30}$-alkyl or $C_{2-30}$-alkenyl, this $R^1$ or $R^2$ can be optionally substituted with 1 to 6 groups independently selected from the group consisting of halogen, —CN, —$NO_2$, —OH, $C_{1-10}$-alkoxy, —O—$CH_2CH_2$O—$C_{1-10}$-alkyl, —O—$COR^3$, —S—$C_{1-10}$-alkyl, —$NH_2$, —$NHR^3$, —$NR^3R^4$, —NH—$COR^3$, —COOH, —COORS, —$CONH_2$, —$CONHR^3$, —$CONR^3R^4$, —CO—H, —$COR^3$, $C_{3-10}$-cycloalkyl, 3-14 membered cycloheteroalkyl, $C_{6-14}$-aryl and 5-14 membered heteroaryl;

wherein $R^3$ and $R^4$ are at each occurrence are independently from each other selected from the group consisting of $C_{1-10}$-alkyl, $C_{2-10}$-alkenyl, $C_{2-10}$-alkynyl, $C_{3-10}$-cycloalkyl, $C_{5-10}$-cycloalkenyl, 3-14 membered cycloheteroalkyl, $C_{6-14}$-aryl and 5-14 membered heteroaryl.

Even more preferably, $R^1$ and $R^2$ are independently from each other $C_{1-30}$-alkyl, wherein $R^1$ or $R^2$ can be optionally substituted with 1 to 6 groups independently selected from the group consisting of halogen, —CN, —$NO_2$, —OH, $C_{1-10}$-alkoxy, —O—$CH_2CH_2$O—$C_{1-10}$-alkyl, —O—$COR^3$, —S—$C_{1-10}$-alkyl, —$NH_2$, —$NHR^3$, —$NR^3R^4$, —NH—$COR^3$, —COOH, —COORS, —$CONH_2$, —$CONHR^3$, —$CONR^3R^4$, —CO—H, —$COR^3$, $C_{3-10}$-cycloalkyl, 3-14 membered cycloheteroalkyl, $C_{6-14}$-aryl and 5-14 membered heteroaryl;

wherein $R^3$ and $R^4$ are at each occurrence are independently from each other selected from the group consisting of $C_{1-10}$-alkyl, $C_{2-10}$-alkenyl, $C_{2-10}$-alkynyl, $C_{3-10}$-cycloalkyl, $C_{5-10}$-cycloalkenyl, 3-14 membered cycloheteroalkyl, $C_{6-14}$-aryl and 5-14 membered heteroaryl.

Most preferably, $R^1$ and $R^2$ are the same and are $C_{1-30}$-alkyl, preferably $C_m$-alkyl, wherein $R^1$ or $R^2$ can be optionally substituted with 1 to 6 groups independently selected from the group consisting of halogen, —CN, —$NO_2$, —OH, $C_{1-10}$-alkoxy, —O—$CH_2CH_2$O—$C_{1-10}$-alkyl, —O—$COR^3$, —S—$C_{1-10}$-alkyl, —$NH_2$, —$NHR^3$, —$NR^3R^4$, —NH—$COR^3$, —COOH, —COORS, —$CONH_2$, —$CONHR^3$, —$CONR^3R^4$, —CO—H, —$COR^3$, $C_{3-10}$-cycloalkyl, 3-14 membered cycloheteroalkyl, $C_{6-14}$-aryl and 5-14 membered heteroaryl;

wherein $R^3$ and $R^4$ are at each occurrence are independently from each other selected from the group consisting of $C_{1-10}$-alkyl, $C_{2-10}$-alkenyl, $C_{2-10}$-alkynyl, $C_{3-10}$-cycloalkyl, $C_{5-10}$-cycloalkenyl, 3-14 membered cycloheteroalkyl, $C_{6-14}$-aryl and 5-14 membered heteroaryl.

In particular, $R^1$ and $R^2$ are the same and are unsubstituted $C_{1-30}$-alkyl, preferably unsubstituted $C_{3-8}$-alkyl such as n-(1-ethyl)propyl.

Also part of the invention, is a process for the preparation of the compound of formula (1)

wherein $R^1$ and $R^2$ are as defined above,
which process comprises the steps of
(i) treating a compound of formula (2) with a boron-containing compound of formula (3) in the presence of a transition metal-containing catalyst to form a boron-containing compound of formula (4)

wherein $R^1$ and $R^2$ are as defined above, and L is a linking group,
and
(ii) treating the boron-containing compound of formula (4) with a cyanide source in order to form the compound of formula (1).

L is preferably $C_{2-5}$-alkylene, which can be optionally substituted with 1 to 6 $C_{1-10}$-alkyl groups. More preferably L is ethylene or propylene and is substituted with 2 to 4 methyl groups.

The transition metal-containing catalyst can be an iridium-containing catalyst such as $[Ir(cod)OMe]_2$, or, preferably, a ruthenium-containing catalyst, such as $RuH2(CO)(PPh_3)_3$.

If the transition metal-containing catalyst is an iridium-containing catalyst, the first step can be performed in the presence of a base such as di-tert-butylbipyridine. If the transition metal-containing catalyst is an iridium-containing catalyst, the first step is usually performed in a suitable organic solvent such as tetrahydrofuran or 1,4-dioxane. If the transition metal-containing catalyst is an iridium-containing catalyst, the first step is usually performed at elevated temperatures, such as at temperatures from 60 to 110° C. In principal, if the transition metal-containing catalyst is an iridium-containing catalyst, the first step can be performed in analogy to the method described by C. W. Liskey; X. Liao; J. F. Hartwig in *J. Am. Chem. Soc.* 2010, 132, 11389-11391, and by I. A. I. Mkhalid, J. H. Barnard, T. B. Marder, J. M. Murphy and J. F. Hartwig in *Chem. Rev.* 2010, 110, 890-931.

If the transition metal-containing catalyst is a ruthenium-containing catalyst, the first step is usually performed in a suitable organic solvent such as toluene, pinacolone and mesitylene or mixtures thereof. If the transition metal-containing catalyst is ruthenium-containing catalyst, the first step is usually performed at elevated temperatures, such as at temperatures from 120 to 160° C.

In one embodiment, the cyanide source in step two can be tetra-$C_{1-10}$-alkylammoniumcyanide, tetra-$C_{1-10}$-alkylphosphoniumcyanide or hexa-$C_{1-10}$-alkylguanidiniumcyanide.

In a second embodiment, the cyanide source in step two can be $Zn(CN)_2$.

The second step is usually performed in the presence of a base such as CsF and a copper reagent such as $Cu(NO_3)_2$. The second step is usually performed in a suitable solvent such as water, methanol and dioxane, or mixtures thereof. The second step is usually performed at elevated temperatures, such as at temperatures from 80 to 120° C.

In principal, if the metal cyanide is $Zn(CN)_2$, step two can be performed in analogy to the method described by C. W. Liskey; X. Liao; J. F. Hartwig in *J. Am. Chem. Soc.* 2010, 132, 11389-11391.

The compounds of formulae (4) and (1) can be isolated by methods known in the art, such as column chromatography.

The compound of formula (2) can be obtained by methods known in the art, for example as described in the subsection titled "Synthesis" of F. Würthner, *Chem. Commun.*, 2004, 1564-1579.

Also part of the invention are the compounds of formula (4)

wherein $R^1$, $R^2$ and L are as defined above.

Also part of the present invention is an electronic device comprising the compound of formula (1) as semiconducting material.

Also part of the invention is the use of the compound of formula (1) as semiconducting material.

Figure 1:
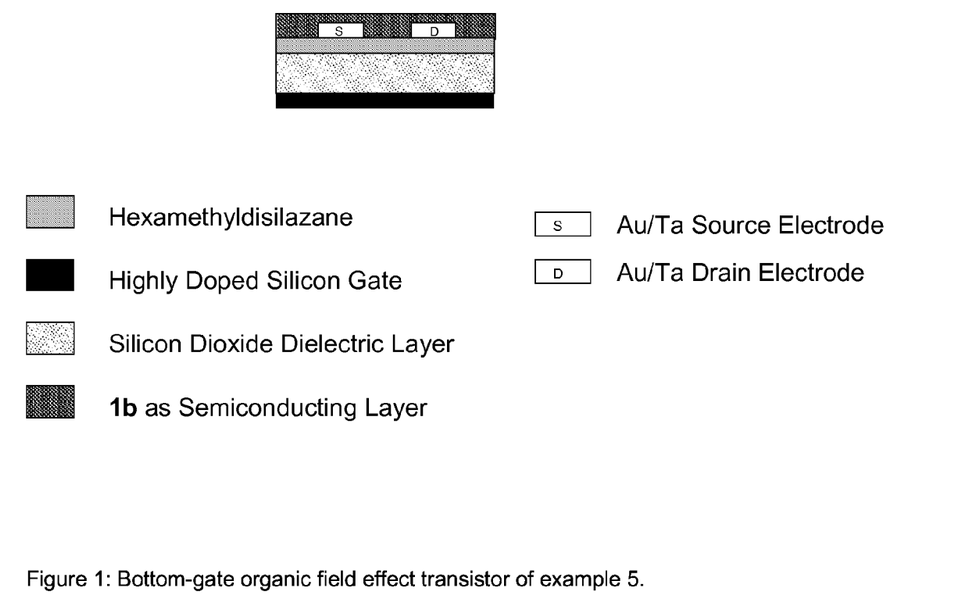

In FIG. 1 the design of the bottom-gate organic field effect transistor of example 5 is shown.

Figure 2:
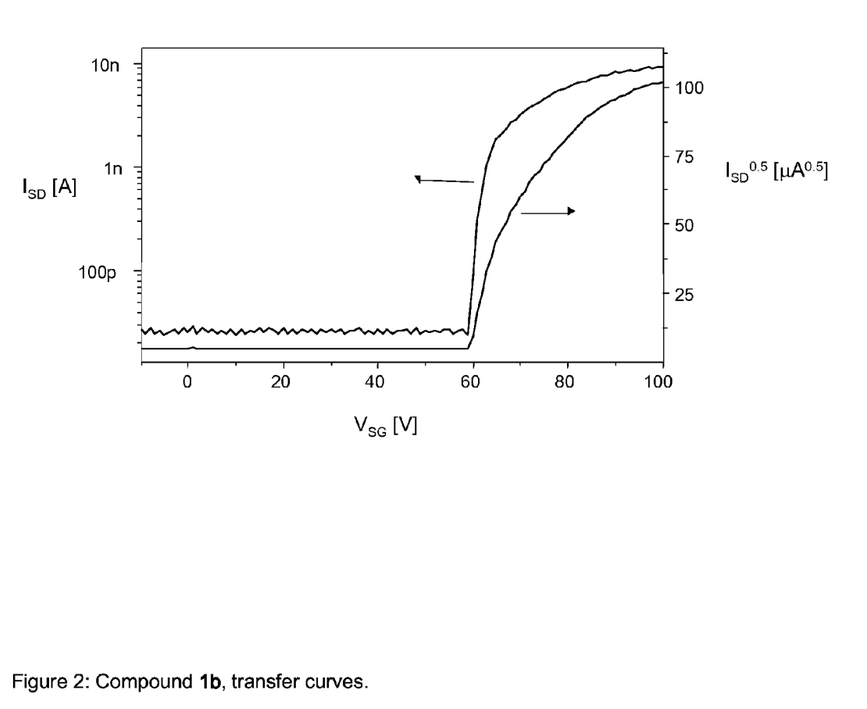

In FIG. 2 the drain current $I_{SD}$ [A] in relation to the gate voltage $V_{SG}$ [V] (top transfer curve) and the drain current $I_{SD}^{0.5}$ [$\mu A^{0.5}$] in relation to the gate voltage $V_{SG}$ [V] (bottom transfer curve) for the bottom-gate organic field effect transistor of example 5 comprising compound 1b as semiconducting material at a drain voltage $V_{SD}$ of 100 V is shown.

Figure 3:
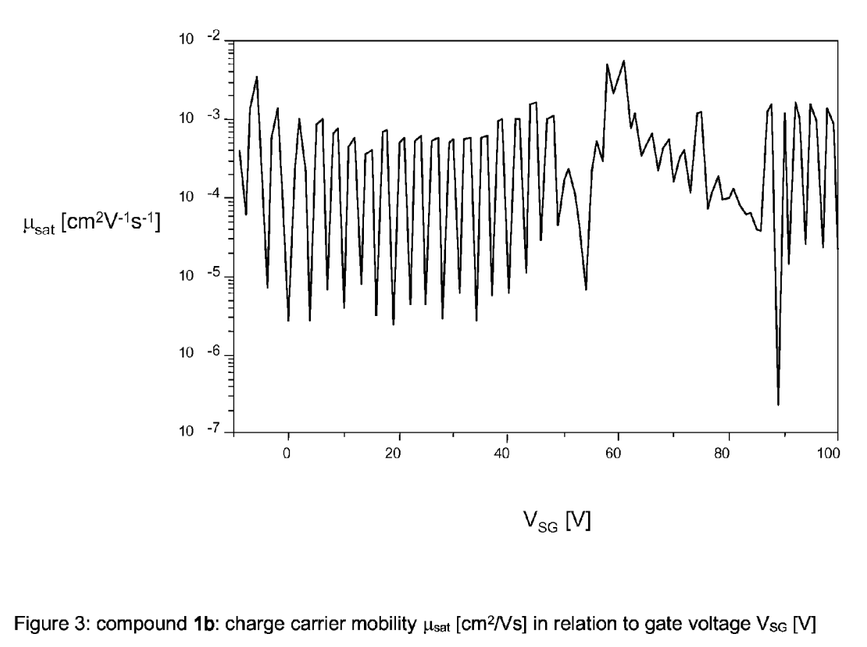
In FIG. 3 the charge carrier mobility μ$_{sat}$ [cm$^2$/Vs] in relation to the gate voltage V$_{SG}$ [V] for the bottom-gate organic field effect transistor of example 5 comprising compound 1b as semiconducting material is shown.

In FIG. 3 the charge carrier mobility $\mu_{sat}$ [cm$^2$/Vs] in relation to the gate voltage $V_{SG}$ [V] for the bottom-gate organic field effect transistor of example 5 comprising compound 1b as semiconducting material is shown.

The compounds of formula (1) show a high charge carrier mobility and a high stability, in particular towards oxidation, under ambient conditions. Furthermore the compounds of formula (1) are compatible with liquid processing techniques.

EXAMPLES

Example 1

Preparation of N,N'-bis(1-ethylpropyl)-2,5,8,11-tetrakis[4,4,5,5-tetramethyl-1,3,2-dioxaborolan-2-y]perylene-3,4:9,10-tetracarboxylic acid bisimide (4a)

N,N'-Bis(1-ethylpropyl) perylene-3,4:9,10-tetracarboxylic acid bisimide (2a) (100 mg, 0.189 mmol) and bispinacolondiboronate (3a) (0.383 g, 1.51 mmol) are mixed together and dissolved in 2 mL dry mesitylene and 0.15 mL dry pinacolone. Argon is bubbled trough the solution for 30 minutes. RuH2(CO)(PPh$_3$)$_3$ (0.082 mg, 0.09 mmol) is added to the reaction mixture and the vessel heated to 140° C. for 30 hours. After cooling the system to room temperature, the solvent is evaporated and the desired compound purified by column chromatography (silica, CH$_2$Cl$_2$/AcOEt 50/1). An orange bright solid is obtained with 60% yield (117 mg, 0.113 mmol).

$^1$H NMR (250 MHz, CD$_2$Cl$_2$) δ 8.59 (s, J=7.3 Hz, 4H), 4.94 (tt, J=9.2, 6.0 Hz, 2H), 2.33-2.10 (m, 4H), 2.04-1.84 (m, 4H), 1.51 (s, J=7.2 Hz, 48H), 0.92 (t, J=7.4 Hz, 12H). FD Mass Spectrum (8 kV): m/z=1033.33 (100%) [M+]. Absorption: 537 nm (in toluene). Emission: 548 nm (in toluene, exc 537 nm). Extinction Coefficient: 7.30×10$^4$M$^{-1}$ cm$^{-1}$. Fluorescence Quantum Yield: 0.89. Elemental Analysis: theoretical: C, 67.34; H, 7.21; N, 2.71; experimental: C, 67.29; H, 7.40; N, 2.96.

Example 2

Preparation of N,N'-bis(1-ethylpropyl)-2,5,8,11-tetracarbonitrile-perylene-3,4:9,10-tetracarboxylic acid bisimide (1a)

N,N'-Bis(1-ethylpropyl)-2,5,8,11-tetrakis[4,4,5,5-tetramethyl-1,3,2-dioxaborolan-2-y]perylene-3,4:9,10-tetracarboxylic acid bisimide (4a) (50 mg, 0.048 mmol), zinc cyanide (68 mg, 0.58 mmol) caesium fluoride (29 mg, 0.19 mmol) and copper nitrate (90 mg, 0.38) are suspended in a mixture of water (1 mL), methanol (1 mL) and dioxane (1 mL). The reaction vessel is closed and heated in microwave for 1 hour at 100° C. The reaction mixture is then poured into a saturated solution of ammonium chloride and extracted with dichloromethane. The organic phase is dried over magnesium sulfate and the solvent evaporated. The product is purified via column chromatography (silica, dichloromethane/acetone 50/1) and obtained as a red-orange solid (yield 40%, 13 mg, 0.019 mmol).

$^1$H NMR (250 MHz, CD$_2$Cl$_2$) δ 8.98 (s, 4H), 5.09 (m, 2H), 2.38-2.16 (m, 4H), 2.11-1.90 (m, 4H), 0.96 (t, J=7.5 Hz, 12H). FD Mass Spectrum (8 kV): m/z=630.9 (100%) [M+].

Absorption: 517 nm (in $CH_2Cl_2$). Emission: 525 nm (in $CH_2Cl_2$, exc 517 nm). Extinction Coefficient: $7.31 \times 10^4$ $M^{-1}$ $cm^{-1}$.

Example 3

Preparation of N,N'-bis(1-heptyloctyl)-2,5,8,11-tetrakis[4,4,5,5-tetramethyl-1,3,2-dioxaborolan-2-y] perylene-3,4:9,10-tetracarboxylic acid bisimide (4b)

N,N'-Bis(1-heptyloctyl) perylene-3,4:9,10-tetracarboxylic acid bisimide (2b) (0.12 mmol) and bispinacolondiboronate (3a) (0.99 mmol) are mixed together and dissolved in 2 mL dry mesitylene and 0.15 mL dry pinacolone. Argon is bubbled trough the solution for 30 minutes. $RuH_2(CO)(PPh_3)_3$ (0.06 mmol) is added to the reaction mixture and the vessel heated to 140° C. for 24 hours. After cooling the system to room temperature, the solvent is evaporated and the desired compound 4b is purified by column chromatography (silica, $CH_2Cl_2$/AcOEt 50/1).

Example 4

Preparation of N,N'-bis(1-heptyloctyl)-2,5,8,11-tetracyano-perylene-3,4:9,10-tetracarboxylic acid bisimide (1b)

N,N'-Bis(1-heptyloctyl)-2,5,8,11-tetrakis[4,4,5,5-tetramethyl-1,3,2-dioxaborolan-2-yl]perylene-3,4:9,10-tetracarboxylic acid bisimide (4b) (63 mg, 0.05 mmol), prepared as described in example 3, cesium fluoride (29 mg, 0.19 mmol), zinc cyanide (68 mg, 0.58 mmol) and copper(II) nitrate 2.5H$_2$0 (89 mg, 0.38 mmol) are suspended in 3 mL of a 5/1 mixture of dioxane/methanol and heated in a microwave vessel at 80° C. for 5 minutes. The reaction mixture is then poured in a saturated solution of ammonium chloride and extracted with dichloromethane. The organic phase is dried over magnesium sulfate and the solvent evaporated. The desired compound is obtained as a brownish solid after column chromatography (silica, dichloromethane) in 40% yield (18 mg, 0.019 mmol). $^1$H NMR (500 MHz, CD$_2$Cl$_2$) δ 8.99 (s, 4H), 5.25-5.14 (m, 2H), 2.30-2.12 (m, 4H), 1.93 (m, 4H), 1.29 (m, 40H), 0.84 (t, J=5.7 Hz, 12H). $^{13}$C NMR (126 MHz, CD$_2$Cl$_2$) δ 161.33 (s), 133.20 (s), 131.01 (s), 129.89 (s), 128.74 (s), 127.35 (s), 117.63 (s), 117.26 (s), 57.17 (s), 32.61 (s), 32.32 (s), 29.97 (s), 29.74 (s), 27.51 (s), 23.16 (s), 14.38 (s). FD/MS (8 kV): m/z=909.9 (100%) [M$^+$]. UV-Vis (in dichloromethane, λ$_{max}$ (∈[M$^{-1}$ cm$^{-1}$]: 518 nm (7.0×10$^4$ M$^{-1}$ cm$^{-1}$). Fluorescence (in dichloromethane, λex=528 nm. φ$_{ex}$: 0.55. Elem. Anal.: theoretical: C, 76.46%, H, 7.30%; N, 9.22%; experimental: C, 76.80%; H, 6.98%; N, 9.50%.

Example 5

Preparation of Bottom-Gate Organic Field Effect Transistors Containing Compound 1b as Semiconducting Material Thermally grown silicon dioxide (thickness: 200 nm) is used as dielectric layer. The gate electrode is formed by depositing highly doped silicon on one side of the dielectric layer. The other side of the dielectric layer is treated with hexamethyldisilazane (HMDS) by vapour deposition of hexamethyldisilazane. The contact angle of the surface of the HMPS-treated side of the dielectric layer is 93.2±1.3°. Source/drain electrodes (Ta (thickness: 10 nm) covered by Au (thickness: 40 nm)) are deposited on the HMPS-treated side of the dielectric layer by vapour deposition. The channel length is 20 μm and the channel width is 1.4 mm, affording W/L=70. The source/drain electrodes are then covered with the semiconducting layer (thickness: ca. 100 nm) by dropcasting a solution of compound 1b in chloroform (concentration=10 mg/mL) in a nitrogen filled glove box (02 content: 0.1 ppm, H$_2$O content: 0.0 ppm, pressure: 1120 Pa, temperature: 17° C.) using a Keithley 4200 machine.

BRIEF DESCRIPTION OF DRAWINGS

The design of the bottom-gate organic field effect transistor of example 5 is shown in FIG. 1.

The drain current I$_{SD}$ [A] in relation to the gate voltage V$_{SG}$ [V] (top transfer curve) and the drain current I$_{SD}$$^{0.5}$ [μA$^{0.5}$] in relation to the gate voltage V$_{SG}$ [V] (bottom transfer curve) for the bottom-gate organic field effect transistor of example 5 comprising compound 1b as semiconducting material at a drain voltage V$_{SD}$ of 100 V is determined in a nitrogen filled glove box (O$_2$ content: 0.1 ppm, H$_2$O content: 0.0 ppm, pressure: 1120 Pa, temperature: 17° C.) using a Keithley 4200 machine. The results are shown in FIG. 2.

The average values and the 90% confidence interval (in parentheses) of the charge carrier mobility μ$_{sat}$ [cm$^2$/Vs], the I$_{ON}$/I$_{OFF}$ ratio and the switch-on voltage V$_{50}$ [V] for the bottom-gate organic field effect transistor of example 5 comprising compound 1b as semiconducting material is given in table 1. The switch-on voltage V$_{50}$ [V] is the gate voltage V$_{50}$ [V] where the drain current I$_{SD}$ [A] starts to increase (out of the off-state).

TABLE 1

| Compound | μ$_{sat}$ [cm$^2$/Vs] | I$_{ON}$/I$_{OFF}$ | V$_{SO}$ [V] |
|---|---|---|---|
| 1b | 1.5 (±1.2) × 10$^{-6}$ | 1.6 (±0.4) × 10$^2$ | 61.3 (±2.0) |

The invention claimed is:

1. A compound of formula (1)

wherein

R$^1$ and R$^2$ are independently selected from the group consisting of H, C$_{1-30}$-alkyl, C$_{2-30}$-alkenyl, C$_{2-30}$-alkynyl, C$_{3-10}$-cycloalkyl, C$_{5-10}$-cycloalkenyl, 3-14 membered cycloheteroalkyl, C$_{6-14}$-aryl and 5-14 membered heteroaryl, wherein if R$^1$ or R$^2$ are C$_{1-30}$-alkyl, C$_{2-30}$-alkenyl or C$_{2-30}$-alkynyl, this R$^1$ or R$^2$ can be optionally substituted with 1 to 6 groups independently selected from the group consisting of halogen, —CN, —NO$_2$, —OH, C$_{1-10}$-alkoxy, —O—CH$_2$CH$_2$O—C$_{1-10}$-alkyl, —O—COR$^3$, —S—C$_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, C$_{3-10}$-cycloalkyl, 3-14 membered cycloheteroalkyl, C$_{6-14}$-aryl and 5-14 membered heteroaryl;

if R$^1$ or R$^2$ are C$_{3-10}$-cycloalkyl, C$_{5-10}$-cycloalkenyl or 3-14 membered cycloheteroalkyl, this R$^1$ or R$^2$ can be optionally substituted with 1 to 6 groups independently selected from the group consisting of halogen,

—CN, —NO$_2$, —OH, C$_{1-10}$-alkoxy, —O—CH$_2$CH$_2$O—C$_{1-10}$-alkyl, —O—COR$^3$, —S—C$_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, C$_{1-10}$-alkyl, C$_{2-10}$-alkenyl, C$_{2-10}$-alkynyl, C$_{6-14}$-aryl and 5-14 membered heteroaryl;

if R$^1$ or R$^2$ are C$_{6-14}$-aryl or 5-14 membered heteroaryl, this R$^1$ or R$^2$ can be optionally substituted with 1 to 6 groups independently selected from the group consisting of halogen, —CN, —NO$_2$, —OH, C$_{1-10}$-alkoxy, —O—CH$_2$CH$_2$O—C$_{1-10}$-alkyl, —O—COR$^3$, —S—C$_{1-10}$-alkyl, —NH$_2$, —NHR$^3$, —NR$^3$R$^4$, —NH—COR$^3$, —COOH, —COORS, —CONH$_2$, —CONHR$^3$, —CONR$^3$R$^4$, —CO—H, —COR$^3$, C$_{1-10}$-alkyl, C$_{2-10}$-alkenyl, C$_{2-10}$-alkynyl, C$_{3-10}$-cycloalkyl, C$_{5-10}$-cycloalkenyl and 3-14 membered cycloheteroalkyl, wherein R$^3$ and R$^4$ are at each occurrence are independently from each other selected from the group consisting of C$_{1-10}$-alkyl, C$_{2-10}$-alkenyl, C$_{2-10}$-alkynyl, C$_{3-10}$-cycloalkyl, C$_{5-10}$-cycloalkenyl, 3-14 membered cycloheteroalkyl, C$_{6-14}$-aryl and 5-14 membered heteroaryl.

2. A process for the preparation of the compound of formula (1) of claim 1, which process comprises the steps of (i) treating a compound of formula (2) with a boron-containing compound of formula (3) in the presence of a transition metal-containing catalyst to form a boron-containing compound of formula (4)

(2)         (3)

(4)

wherein R$^1$ and R$^2$ are as defined in claim 1, and L is a linking group, and

(ii) treating the boron-containing compound of formula (4) with a cyanide source in order to form the compound of formula (1).

3. The process of claim 2, wherein in the compound of formula (4) L is C$_{2-5}$-alkylene, which can be optionally substituted with 1 to 6 C$_{1-10}$-alkyl groups.

4. The process of claim 2, wherein the cyanide source in step (ii) is selected from the group consisting of tetra-C$_{1-10}$-alkylammoniumcyanide, tetra-C$_{1-10}$-alkylphosphoniumcyanide and hexa-C$_{1-10}$-alkylguanidiniumcyanide.

5. The process of claim 2, wherein the cyanide source in step (ii) is Zn(CN)$_2$.

6. A compound of formula (4)

wherein R$^1$, R$^2$ are as defined in claim 1 and L is a linking group.

7. An electronic device comprising the compound of formula (1) of claim 1 as semiconducting material.

8. A compound according to claim 6, wherein L is C$_{2-5}$-alkylene, which can be optionally substituted with 1 to 6 C$_{1-10}$-alkyl groups.

* * * * *